United States Patent [19]

Sandland

[11] 4,334,154
[45] Jun. 8, 1982

[54] TOMOGRAPHIC SCANNING APPARATUS

[75] Inventor: Paul Sandland, Half Moon Bay, Calif.

[73] Assignee: General Electric Company, Milwaukee, Wis.

[21] Appl. No.: 943,076

[22] Filed: Sep. 18, 1978

Related U.S. Application Data

[60] Division of Ser. No. 856,946, Dec. 2, 1977, Pat. No. 4,236,079, which is a continuation of Ser. No. 667,938, Apr. 19, 1976, abandoned.

[51] Int. Cl.³ .............................................. A61B 6/00
[52] U.S. Cl. ................................. 250/445 T; 250/207
[58] Field of Search .................... 250/207, 445 T, 388

[56] References Cited

U.S. PATENT DOCUMENTS

| | | | |
|---|---|---|---|
| 3,514,209 | 5/1970 | McGhee et al. | 250/207 |
| 3,562,795 | 2/1971 | Frenk | 250/207 |
| 4,035,647 | 7/1977 | Hounsfield et al. | 250/445 T |
| 4,190,772 | 2/1980 | Dinwiddie et al. | 250/445 T |

Primary Examiner—Alfred E. Smith
Assistant Examiner—T. N. Grigsby
Attorney, Agent, or Firm—Dana F. Bigelow; Douglas E. Stoner

[57] ABSTRACT

Scanning apparatus is disclosed for use in computerized axial tomography systems. The apparatus includes an assembly rotatable about an axis extending along a central opening defined therein, and means for positioning the body portion to be examined within the central opening so that the axis of assembly rotation is perpendicular to a plane passing through the bodily structures to be examined. A source of penetrating radiation is mounted on the assembly toward one side thereof and provides radiation in the form of a fan beam. Detector means for the radiation are positioned on the assembly opposite the source, enabling detection of radiation which traverses laterally and is not absorbed in the thin body section in which the aforementioned plane resides. Means are provided for rotating the assembly so that the fan beam impinges upon said body portion at a plurality of incident directions. Signal processing and conditioning means mounted on the assembly and movable therewith, receive the output signals from the detector means and amplify and convert same to digital form. Slip ring interconnection means rotatable with the assembly, receive the outputs from the signal processors and conditioners and interfeed these signals to a computerized image reconstruction station. Slip rings rotatable with the assembly also provide interconnection enabling power and control inputs to the radiation source and to other portions of the apparatus. The assembly is continuously rotatable through successive 360 degree rotations and the examination sequence may be initiated at any point in the rotation of the assembly. The detector comprises an array of elements and means are provided for adjusting the gains of each channel associated with the individual detector elements as an incident of the examination process, thereby enabling compensation for drift in the channels.

1 Claim, 7 Drawing Figures

FIG. 7

TOMOGRAPHIC SCANNING APPARATUS

This is a division of application Ser. No. 856,946 filed Dec. 2, 1977 and now U.S. Pat. No. 4,236,079, which is a continuation of Ser. No. 677,938, filed April 19, 1976, now abandoned.

BACKGROUND OF INVENTION

This invention relates generally to medical diagnostic apparatus and methodology, and more specifically relates to x-ray scanning apparatus of the type utilized in computerized tomography.

Within very recent years, a relatively enormous degree of interest has been evidenced on the past of medical diagnosticians in a field now widely known as computerized tomography. In a typical procedure utilized in computerized tomography (or CT), an x-ray source and detector means are positioned on opposite sides of the portion of the patient which is to be examined. In the prior art these paired elements are made to transit across the body portion to be examined, while the detectors measure the x-ray absorption at the plurality of transmission paths defined during the transit process. Periodically as well, the paired source and detector means are rotated to a differing angular orientation about the body, and the transit process repeated. A very high number of absorption values may be yielded by procedures of this type, and the relatively massive amount of data thus accumulated may be processed by a digital computer—which cross-correlates the absorption values to thereby derive absorption values for a very high number of points (typically in the thousands) within the section of the body being scanned. This point by point data may then be combined to enable reconstruction of a matrix (visual or otherwise) which constitutes an accurate depiction of the density function of the bodily section examined. The skilled diagnostician, by considering one or more of such sections, may diagnose various bodily elements such as tumors, blood clots, cysts, hemorrhages and various abnormalities, which heretofore were detectable, if at all, only by much cumbersome and, in many instances, more hazardous (from the viewpoint of the patient) techniques.

While apparatus of the aforementioned type have therefore represented powerful diagnostic tools, and have been deemed great advances in the radiography art, apparatus heretofore designed and commercially available have suffered from many of the shortcomings incident to first generation devices. Thus, for example, it may be noted that acquisition of the raw data obtained as an incident of the discussed techniques frequently entailed an undesirably long period—in which among other things subjected a patient to both inconvenience and stress. The patient's inability to remain rigid for such a lengthy period, also could lead to blurring of the image sought to be obtained.

The prior art apparatus furthermore is not well adapted to successive use with a large number of patients. For example, to the extent rotational scanning has been utilized, such apparatus has in general been designed to effect a single rotational cycle, with intertransmission of the various excitation potentials for the x-ray tube, and the signal outputs for the detectors being effected through means which are not compatable with continuously rotating configurations. Aside from the inconvenience, inefficiency and delays that are incident to stopping and starting of the equipment, such procedures can adversely affect system components. For example, the spinning anodes used in many X-ray tubes possess a very high moment of inertia in consequence of their rapid rotation, and this augments the stresses imposed on such elements by sudden velocity changes in their reference frame.

Such prior devices furthermore have not been markedly adapted to use in rapidly producing a consecutive series of cross-sectional views through a patient, or portion of a patient being examined.

In other instances, the amount of radiation received by the patient during examination was excessive—due to certain failings in the types of X-ray techniques and procedures utilized.

In an equally significant aspect of the prior art devices, it has been observed that the picture (or output data) quality resulting from use of such devices was less than fully acceptable—particularly where data is obtained over an extended period. A principal cause of this difficulty is the fact that such apparatus are indeed utilized over the course of an extended period, e.g. as is the practice in use of these devices in large institutional environments. During the extended periods incident to such use, temperature and/or time-generated drifts in the electronic processing circuits, i.e., the circuits utilized with the detectors, can cause changes among the various processing channels, with resultant introduction of erroneous information into the signal outputs provided to the computer.

In a copending application of John M. Pavkovich and Craig S. Nunan, Ser. No. 643,894 filed on Dec. 23, 1975 entitled "Tomographic Apparatus and Method for Reconstructing Planar Slices from Non-absorbed Radiation", and as well in the similarly copending application of John M. Pavkovich entitled "Apparatus and Method for Reconstructing Data", filed on Dec. 23, 1975, under Ser. No. 643,896, both applications of which are assigned to the same assignee as is the present application, apparatus and methodology are disclosed which alleviate certain of the aforementioned problems, most notably including the lengthy period that has heretofore been involved in computer processing of the raw data provided by the detectors. The apparatus therein disclosed utilizes a fan beam source of radiation coupled with application of a convolution method of data reduction, with no intervening reordering of fan rays, to thereby eliminate the errors and delays in computation time which would otherwise be involved in such reordering. The radiation source and the detector means are positioned on opposite sides of the portion of the patient to be examined and these elements are made to rotate through a revolution or portion thereof while the detectors measure the radiation absorption at the plurality of transmission paths defined during the rotational process.

In accordance with the foregoing, it may be regarded as an object of the present invention to provide scanning apparatus for use in computerized tomography systems or the like, which is adapted to rapid and virtually continuous use in diagnostic treatment of a series of patients, and which, by virtue of the continuous operation thereof, avoids the physical stressing of system components which can result as an incident of starting and stopping of the rotatable assemblies utilized with such apparatus.

It is a further object of the present invention to provide apparatus of the aforementioned type which is adapted for use in producing a series of successive cross-sectional views through a portion of a patient being examined.

It is a yet further object of the present invention, to provide apparatus of the aforementioned type wherein the quality of the data generated, and therefore the resulting capabilities for image reconstruction, can be markedly improved by incorporation of calibration circuitry, which enables compensation to be effected for drift in the electronic processing circuits resulting from temperature or time-induced changes in circuit components.

It is a still further object of the invention, to provide scanning apparatus for use in computerized tomography systems or the like, wherein the signal processing and conditioning circuitry is in close physical proximity to the detector elements on the rotating assembly of the apparatus, thereby minimizing noise and spurious signals, as may, e.g. be induced by the circuitry associated with the radiation source used in the apparatus.

It is a yet additional object of the present invention, to provide scanning apparatus for use in computerized axial tomography systems, which includes interconnection means movable with the portion of the said apparatus subject to rotation, whereby the various signal information proceeding to the reconstruction and control station and, as well, the power and control signals for the radiation source, may be interfed to and from the rotating portions of the apparatus in simple and effective fashion, and without any requirement for periodically stopping or reversing system rotation.

SUMMARY OF INVENTION

Now in accordance with the present invention, the foregoing objects, and others as will become apparent in the course of the ensuing specification, are achieved in a scanning apparatus which includes an assembly rotatable about an axis extending along a central opening defined therein, and means for positioning the body portion to be examined within the central opening so that the axis of assembly rotation is perpendicular to a thin, generally planar section of the body portion to be scanned. A source of penetrating radiation, as for example, of x-rays of gamma rays, is mounted on the assembly toward one side thereof and provides radiation in the form of a fan beam. Detector means for the radiation are positioned on the assembly opposite the source, enabling detection of non-absorbed radiation proceeding laterally across the section. Means are provided for rotating the assembly so that the fan beam impinges upon the body portion at a plurality of incident directions.

Signal processing and conditioning means are mounted on the rotatable assembly and are movable therewith, for receiving the output signals from the closely adjacent detector means. The signal processing and conditioning means amplify and convert the signals provided thereto, to digital form.

Slip ring interconnection means rotatable with the aforementioned assembly, receive the outputs from the signal processing and conditioning means and enable interfeed of these signals to a computerized control and image reconstruction station. The said interconnections also permit receipt and interfeed of control signals from the central control logic, and switching etc. present at the aforementioned station.

Further slip ring means are also provided, which are rotatable with the aforementioned assembly, these providing interconnections enabling power and control inputs to the radiation source, i.e. typically to the x-ray tube.

The aforementioned assembly is continuously rotatable through successive 360 degree rotations or less, and the examination sequence may be initiated at any selected point in the rotation of the assembly.

The detector means preferably comprises a plurality or array of discrete elements, and means are provided for adjusting the relative gains of the channels associated with the detector elements—as an incident of the patient examination process. This enables compensation to be effected for drift in the said channels, which may typically arise, e.g. from time or temperature-induced changes in circuit components.

BRIEF DESCRIPTION OF DRAWINGS

The invention is diagrammatically illustrated, by way of example, in the drawing appended hereto, in which.

DESCRIPTION OF PREFERRED EMBODIMENT

Figure 1:
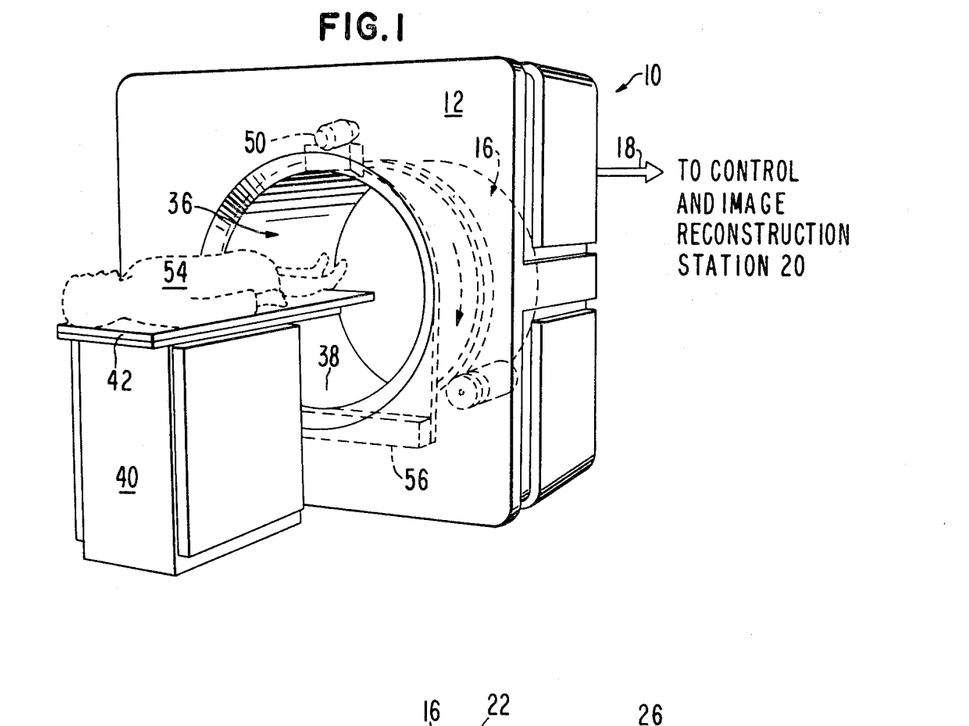
FIG. 1 is an external perspective view, somewhat schematic in nature, of scanning apparatus in accordance with the present invention.

In FIG. 1 herein an external perspective view appears, the view being somewhat simplified in nature and setting forth scanning apparatus 10 in accordance with the invention. This view may be considered simultaneously with the views of FIGS. 2 and 3. Apparatus 10 is seen to comprise generally an external casing 12 within which a frame 14 (FIG. 3) supports a rotatable assembly 16, which assembly is better seen in FIG. 2. Scanning apparatus 10 forms part of a computerized tomography system, the remaining elements of which will be further described in connection with FIG. 4, and which principally include control, image reconstruction elements, and image display elements, most of which are contained at a control and image reconstruction station generally designated at 20. Apparatus 10 is in communication with station 20 via various control lines as schematically indicated at link 18 in FIG. 1, which is to say that digital information obtained in consequence of the scanning operations effected by apparatus 10 are furnished to station 20; and the latter, in turn, provides both control information for actuating apparatus 10, as well as the various power and excitation potentials, e.g. for the radiation source, the motor, and other elements which are present in apparatus 10.

Figure 2:
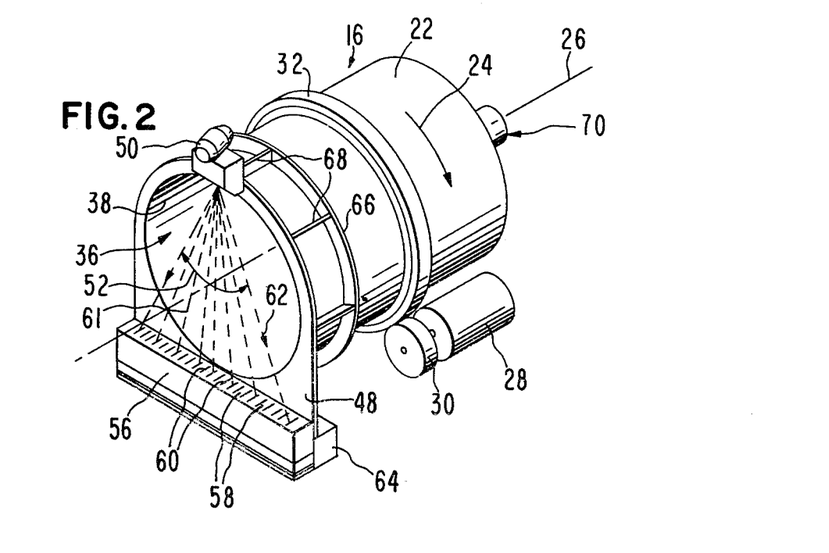
FIG. 2 is a perspective view, again somewhat schematic in nature, depicting the rotatable assembly portion of the FIG. 1 apparatus.

Rotatable assembly 16 includes an outer cylinder 22 of stainless steel or other metal, and is adapted to be rotated in direction 24 about its central axis 26, by means of a motor 28, the drive wheel 30 of which bears against a drive collar 32 which is secured about cylinder 22. Wheel 30 may thus include a rubber surface 34 or the like, which by virtue of its high coefficient of friction, is effective in causing non-slip rotation of cylinder 22.

By comparing FIGS. 1 and 2 it will be evident that the central opening 36 of rotatable assembly 16 serves to receive a patient 54 who is to be examined within apparatus 10. A sleeve 38 of plastic or the like is secured to casing 12, and provides a stationary reference frame which has certain advantages—especially psychologically for the patient who is positioned within opening 36.

The patient 54 during use of apparatus 10 is positioned upon the top surface 42 of a positioning bench 40, the surface 42 being movable along axis 26 so as to enable movement of patient 54 into the apparatus. A laser source 44 is positioned in front of apparatus 10 at an overhead position (FIG. 3) so that the beam 46 thereof impinges upon the patient at an axial location—to aid in proper alignment of the patient during the examination process. The laser may also be affixed to portions of casing 12. The bench 40 may include actuating means which will be further discussed in connection with FIG. 4, which enable incremental advance of same, so as to facilitate successive transverse scan sections through the body of patient 54 and which also enable movement of the bench in other directions to facilitate patient positioning.

The forward end of assembly 16 carries a plate 48, at the periphery of which is mounted a radiation source 50—preferably comprising an X-ray source capable of projecting an X-ray pattern in the form of a fan beam 52. Fan beam 52 may be yielded by collimators (not shown) which are positioned in front of the X-ray emission source—as is known in the art. Fan beam 52 is preferably (though not necessarily) at least as wide as the object to be examined, which is the present instance, of course, constitutes patient 54.

A detector means, generally indicated at 56 is mounted directly opposite source 50, i.e. toward the opposite edge of plate 48. The detector means preferably comprises an array of ionization chambers, such as xenon-krypton detectors, although other types of detectors suitable for use with X-rays and similar electromagnetic radiation may be utilized, such as crystal scintillators coupled with photomultipliers or photodiodes or so forth. Individual cells 58 of the detector array are separated by collimator plates 60; the plates and cells are oriented with increasing inclination toward source 50 as one proceeds toward the ends of the array, i.e. so that a ray such as ray 62 actually is incident on the pertinent cell along the axis of such cell.

In accordance with one important aspect of the present invention, detector means 56 is in very close physical proximity to a signal processing and conditioning means, generally indicated at 64. Indeed, in the apparatus depicted these two blocks are back to back with respect to one another. This close physical proximity has important advantages in the present environment in that the close proximity of these elements—which are commonly rotatable with assembly 16—minimizes the possibility of introducing spurious signals into the various detector channels. This is particularly significant in the present instance in that the high potentials associated with the X-ray source etc. increases the likelihood of introducing such spurious signals.

The assembly 16 in addition to including the several elements thus far described, includes certain strengthening elements such as the reinforcing ring 66 and cross braces 68. The purpose of these several elements is to increase, to the extent practical, the rigidity of the overall assembly 16, thereby decreasing the effects of vibration and the possibility of undesired flexure, all of which can be particularly detrimental with respect to the detector structures—i.e., stressing of certain of these structures can change the electrical response characteristics of same, thereby introducing erroneous readings.

In the case of X-ray diagnosis the thickness of fan beam 52 as defined by the collimators is typically between 1 mm and 15 mm at the middle of the object. It will be understood that as the source-detector array undergoes relative rotation with respect to the patient (continuously where exact reconstruction is desired) over a time of approximately 1 to 15 seconds, readings of absorbed radiation are measured by detector means 56. The data acquisition may be completed during one relative revolution (i.e. 360 degrees) of the system; the present system is also well adapted to acquire the data over the course of several revolutions—which can provide superior images because of the increased quantity of data. As further described in the aforementioned copending application of Pavkovich, et al., Ser. No. 643,894, data from detector means 56, after suitable processing and conditioning, is provided to station 20 where it is convolved, appropriately stored and later back-projected with other data to produce an output picture which is a replica of the thin cross-section of patient 54 which has been examined. It will of course be understood that the data need not be necessarily converted into a visually discernable picture; but can be expressed in other analytical forms, i.e. numerically or so forth.

Figure 3:
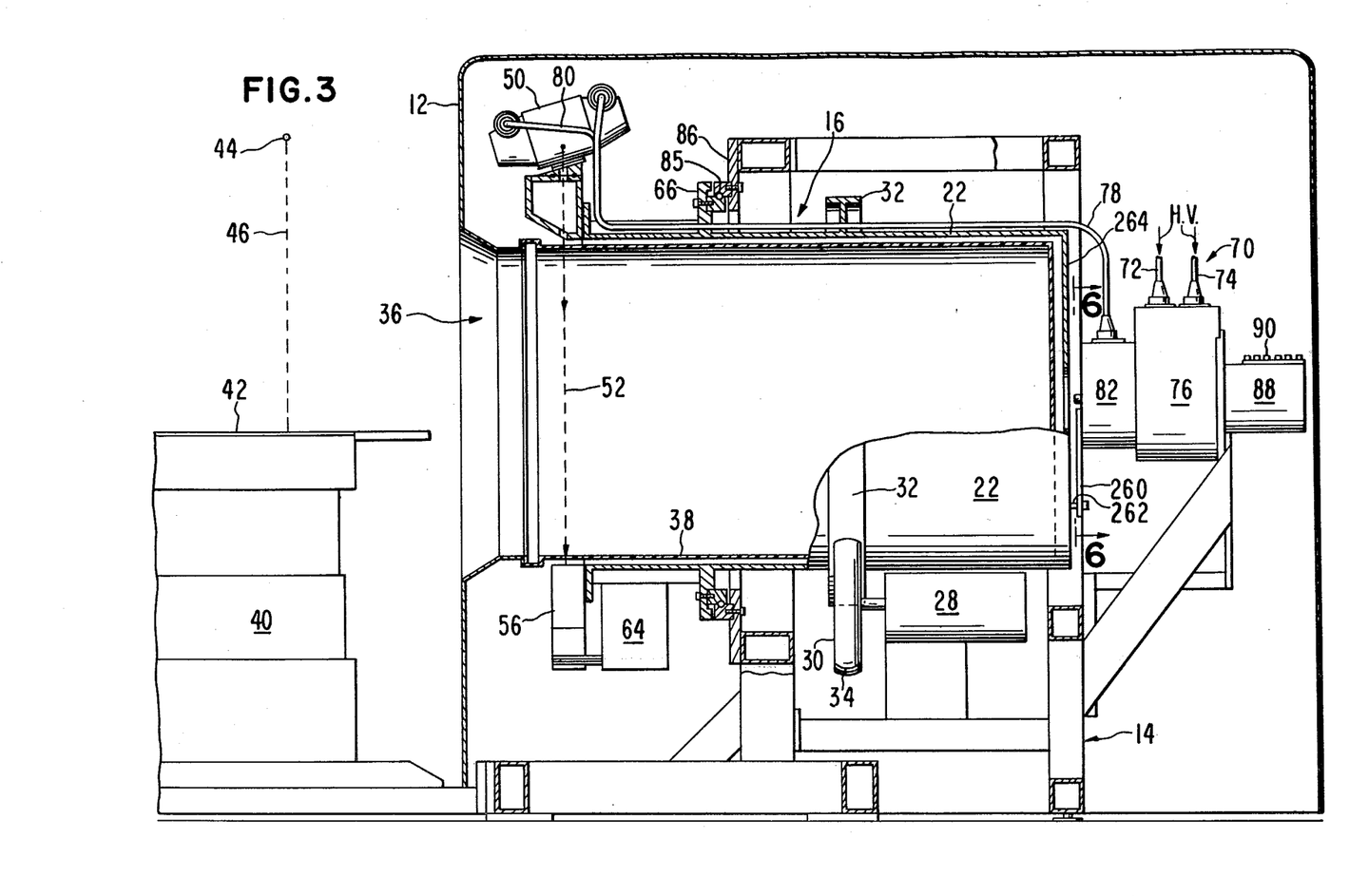
FIG. 3 is a side elevational view of the apparatus of FIGS. 1 and 2 herein, the view being partially broken-away and sectioned.

In accordance with a further aspect of the present invention and as may initially be seen by consideration of FIG. 3, electrical interconnections to all portions of assembly 16 which requires same, is effected via a slip ring assembly, which is generally indicated at 70. In particular it will be observed that high voltage input lines 72 and 74 are provided to the casing portion 76 of assembly 70, which portion is stationary. The slip ring interconnection scheme subsequently to be discussed in connection with FIGS. 6 and 7 then provide the required excitation connections to X-ray source 50 via the cables 78 and 80 which proceed from casing portion 82 of assembly 70. The latter, portion 82, rotates with rotating assembly 16, which is supported on bearing 85 between ring 66 and a frame ring 86.

Similarly the various further low voltage interconnections, i.e. for the detector outputs for the various low voltage control signals for the electrical elements mounted on plate 48, and for the low voltage inputs to source 50 (for the anode rotor), are all enabled by means of slip ring connections contained within portion 88 of slip ring assembly 70. Thus several of the external connections 90 appear at portion 88, the external casing of portion 88 is, of course, stationary. Further details regarding slip ring assembly 70 will, as already mentioned, be discussed in connection with FIGS. 6 and 7 hereinbelow.

Figure 4:
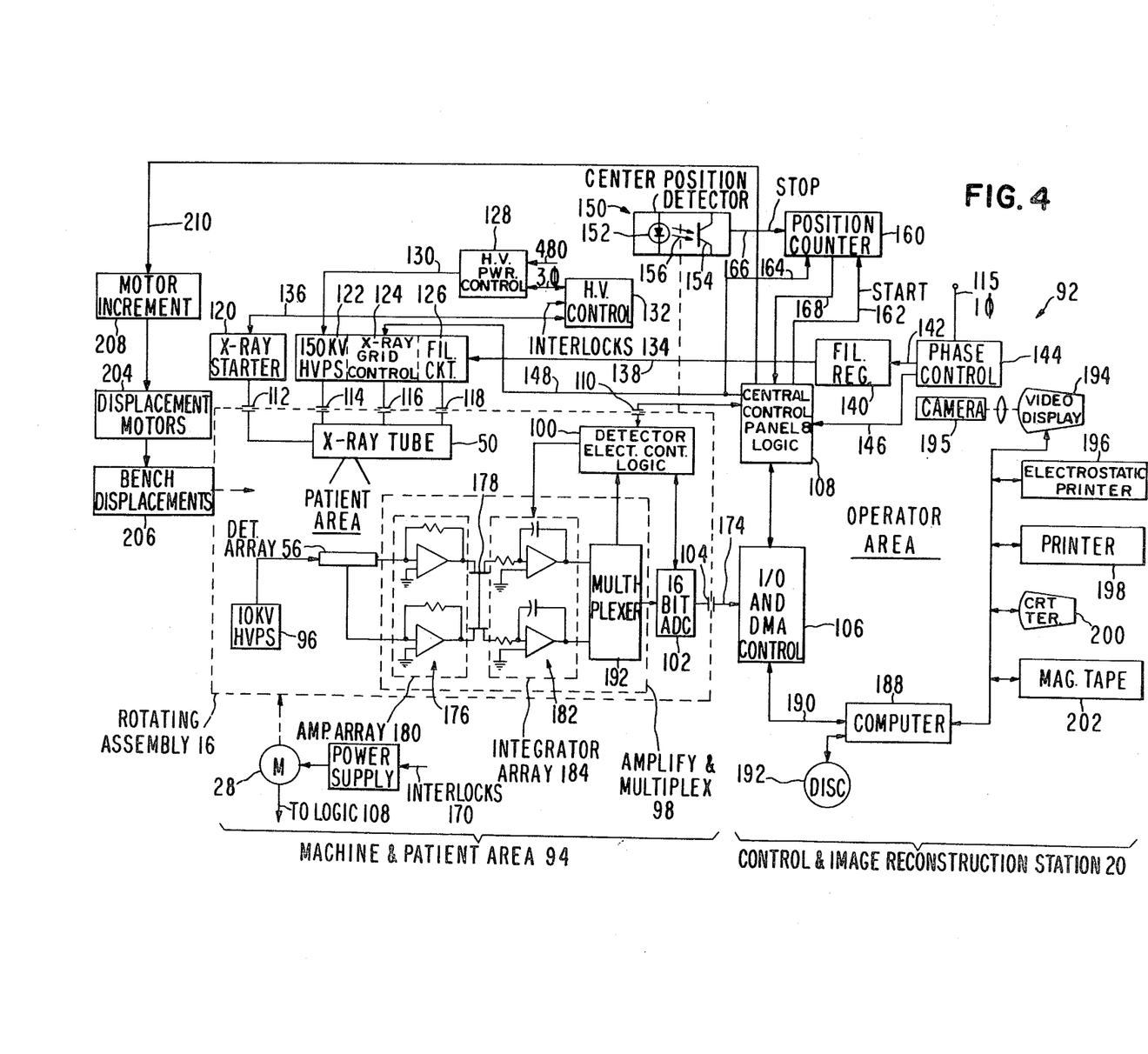
FIG. 4 is a simplified electrical block diagram setting forth the control and circuit elements utilized in the apparatus of FIGS. 1, 2 and 3; the said view, further, illustrates interaction of the elements in the said apparatus with the remaining portions of a computerized tomography system in which the apparatus is incorporated.

In FIG. 4 herein an electrical schematic block diagram appears setting forth the interrelationship of the various elements present in apparatus 10; the figure also depicts the relationship between apparatus 10 and its associated elements, with the various operative elements in the overall computerized axial tomography system 92, with which apparatus 10 may be utilized.

The tomography system 92 is thus seen to generally include a machine and patient area 94, which includes those elements thus far depicted in connection with FIGS. 1 through 3, and a control and image reconstruction station 20 which communicates with the machine and patient area.

Those portions of the overall system 92, which are mounted to and movable with rotating assembly 16 are generally designated within the dotted line identified by this same reference numeral 16. These thus include the detector array 56; the radiation source 50 in the form of an X-ray tube; a high voltage power supply 96 which provides required potential for the detector array 56; an amplify and multiplex block 98 which processes the various signal channels proceeding from detector array 56, detector electronics control logic 100; and an analog-to-digital converter 102 for receiving the output from block 98 and furnishing same in digital form for transmission to control and image reconstruction station 20.

All interconnections to rotating assembly 16 are effected through slip rings, as has previously been mentioned. Thus, in particular, the output from the ADC 102 is provided via a slip ring assembly 104 to an input-/output and direct memory access control means 106. Similarly the interconnection between central control panel and logic 108, which is at station 20, and the detector electronic control logic 100 is via the slip ring assembly 110. Similarly all power and excitation potentials to X-ray tube 50 are provided via a series of slip rings 112, 114, 116 and 118, which respectively connect the X-ray starter 120 (i.e. to initiate anode rotation and continuation of same); the high voltage potential from power supply at 122, the X-ray grid control 124, and the filament circuit power supply 126.

The various power inputs for X-ray tube 50 etc. originate at stationary and essentially conventional devices of this sort which are present at control and image reconstruction station 20 or are present in machine and patient area 94, but which do not form part of rotating assembly 16. Thus, in particular a high voltage power control 128 is provided, which furnishes control via line 130 to high voltage power supply 122. Both of these elements, as mentioned, are external to rotating assembly 16. A high voltage control 132 is in communication with the high voltage power control 128, and interlocks, as is known in the art, are provided as schematically suggested at 134. The same high voltage control at 132 also controls actuation of X-ray starter supply 120 through the control line 136. The filament circuits 126 are provided with power through line 138, via regulating means 140, which in turn receives its power through the input line 142 via phase control 144. Such phase control is useful in connection with filament excitation, in order to avoid an uneven temperature distribution at same.

The phase control 144 also provides an input via line 146 to central control logic 108. This input is used in correlating actuation of the X-ray grid-control 124, i.e. via line 148 in accordance with the phasing of line current. The X-ray grid-control 124 periodically provides pulses to the X-ray tube grid during a cycle of operation of the present apparatus in order to effect X-ray emission in pulse form. The X-ray pulses in particular are typically provided at a rate of one such pulse for each degree of rotation of assembly 16—although it is possible to provide 2 or more pulses for each degree of rotation; or other pulsing schemes can be used.

In accordance with an important aspect of the present invention, it will be appreciated that the use of slip rings for all interconnection purposes obviates any requirement for periodically stopping rotation of assembly 16. Indeed in a preferred mode of operating the present device, the rotation of the said assembly 16 may be continously maintained. For example, such rotation may be continued while a series of sectional scans are run upon a single patient; or the rotation may be continued while scans or series of scans are run upon successive patients. This has an important advantage, not only in terms of the saving of time and minimizing of operations, but moreover this aspect of the operation eliminates mechanical stresses which could otherwise be imposed upon system components by virtue of stopping and starting of the assembly. This includes stresses that could be thus imposed upon the very heavy structural components of the assembly; stresses that could be imposed upon the rapidly rotating anode portion of the X-ray tube; and vibrational stresses that are particularly detrimental to the detectors.

A 360 degree scan is initiated by the operator inserting such request at central control panel and logic 108. Since, as mentioned, the rotation may be effected continuously, it is also desirable to be able to initiate the scanning cycle with respect to a patient at any point in the rotation of assembly 16, i.e. irrespective of the particular angular setting at the time the sequence is initiated. This is significant for the following reason: In a typical mode of operation of the present device an entire 360 degree scan, i.e. a full rotation of assembly 16 may be effected within 1 to 6 seconds. This is an extremely rapid period, especially vis-a-vis the much longer periods that have been utilized in the prior art for such purposes. During such scan cycle, however, it is desirable, (if not necessary) that the patient hold his breath to avoid any possibility of image blurring. Were it only possible for the scanning cycle to be initiated at a single point in assembly 16 rotation it would be conceivable that the cycle initiation could be effected in such a manner that scanning would not begin for as long as 6 seconds from operator initiation so that the total time in which the patient would be required to hold his breath could be 12 seconds—which is relatively undesirable, especially where enfeebled patients are being examined. For such reason, in the present device a center position detector 150 is provided, which comprises a simple optically coupled switch including a light emitting source 152 (e.g. an LED) and a light sensitive receptor, such as phototransistor 154. A projection mounted to plate 48 (schematically indicated at 156), and rotatable therefore with assembly 16, intersects the light path between source 152 and receptor 154 once during each assembly rotation. The output from detector 150 at line 166 is provided to a position counter 160. Upon a scan cycle being initiated at central control panel and logic 108, a start signal proceeds through line 162 which starts counter 160. During the continuing rotation, the pulse control signals provided by logic 108 to grid control 124 are also provided via line 164 to position counter 160. Upon the center position being reached, projection 156 intersects the light path at detector 150 and a STOP signal is provided to counter 160 via line 166. The count in counter 160 is then provided via line 168 to logic 108. From this count logic 108 determines a stream of information indicating the absolute angular position for each set of scanned data obtained by the detectors during the scan operation. Rotation of assembly 16 is enabled as already discussed, by the motor 28, which may be provided with interlocks 170. The motor is actuated and deactuated under influence of central control panel and logic 108.

Detector array 56 in a typical instance may include 301 separate detector elements, in turn providing 301 output signals, which are all at a very low analog level. A series or array of corresponding signal processing and conditioning channels are utilized to amplify and integrate these signals and provide same to a multiplexer 192, which multiplexes the signals in time and provides same to an analog-to-digital converter 102. By the use of these techniques the large number of input signals from the detectors may be sufficiently reduced, so that a relatively small ADC, i.e. a 16-bit ADC may be utilized, whereupon a single output line 174 may interfeed the stream of data from a large number of channels. Thus a relatively small number of output lines such as 174 may be used to interfeed the data from assembly 16 to the control and image reconstruction station 20. It of course will be appreciated here that only two of the several hundred channels actually are shown in FIG. 4. In actual practice e.g. twenty or so lines such as at 174 can be typically used with a totality of 301 channels.

In the circuitry illustrated in FIG. 4 the amplifier array 180 may consist of a plurality of operational amplifiers 176, with a series of FET switches 178 gating the outputs from the amplifiers to a series of integrators 182 forming part of an integrator array 184.

The various operations performed at the detector signal processing and conditioning channels are effected under control of logic 100. The detector signals after being amplified and integrated to increase their level, are thereupon time-multiplexed at multiplier 192, which considerably reduces the requirements for transmission channels, and as mentioned then furnishes the multiplexed signals to analog-to-digital converter 102, with the data thereupon being passed through slip ring 104 to input/output and direct memory access control means 106 which is in communication with a computer 188 via the line 190. The detector data may then be stored at appropriate memory points, e.g. in disc 192 or in other memory elements associated with the computer. Computer 188 is preferably a digital computer of a type suitable and known for use in purposes such as the present application.

Various additional elements useful in displaying and processing the information furnished to computer 188 may be associated with the tomographic system 92, including a video display 194 (which may be coupled with a camera 195), an electrostatic printer 196, a printer 198, a CRT terminal 200, and magnetic tape recording means 202. The operation of all of the elements cited, is per se well known in data processing systems, and therefore it is not deemed necessary to discuss in detail aspects of same.

In order to enable a series of successive transverse sections to be scanned at patient 54, it has been mentioned that the bench surface 42 may be provided with means to effect incremental advance of same in an axial direction toward opening 36—and also for displacing surface 42 in other directions for achieving proper patient orientation. As is indicated in FIG. 4, this may be effected in a simple manner by the displacement motors 204, which actuate bench displacement means 206. Motors 204 are incremented through a motor increment means 208, in turn periodically actuated by central control logic 108 via control line 210; i.e. at the end of each rotational scan a signal proceeds from central control logic 108, which causes the displacement motors to undergo a stepped movement—which through mechanical linkages effect incremental displacements of bench surface 42—e.g. to incrementally advance surface 42 into opening 36.

Referring momentarily to FIG. 2, it will be appreciated that during the course of a patient scan, the outer rays of fan beam 52, such as ray 62, will typically pass through less tissue in the patient than will more central rays such as 61. As an alternative to or in addition to inserting physical compensators (i.e. radiation absorbers), and in order to improve the performance of the signal conditioning and processing channels, the various detector signal channels can be provided with differing gain characteristics, e.g. by utilizing resistors of differing values in the gain channels. In consequence, the channels associated with the detector for outer rays such as ray 62 will have lesser gain than those processing the signals arising from the highly absorbed central rays as ray 61.

Figure 5:
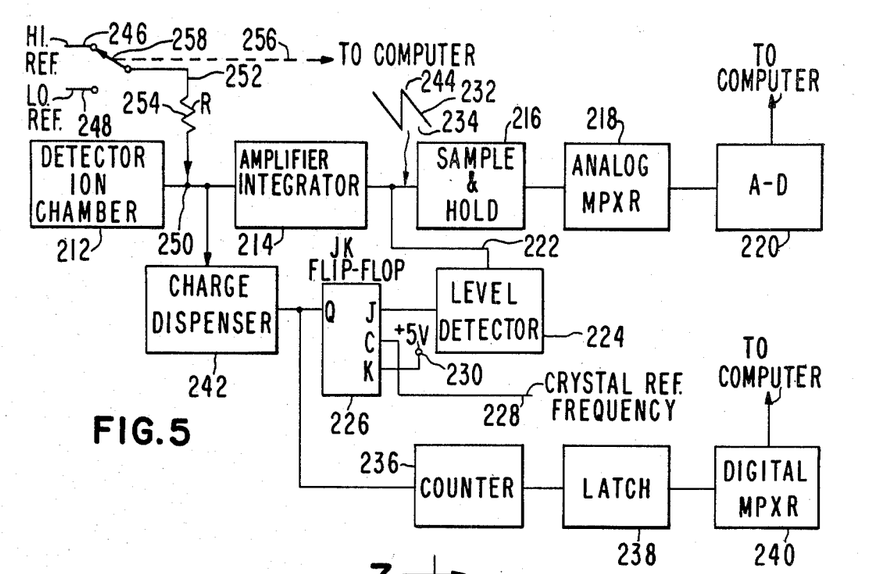
FIG. 5 is an electrical schematic block diagram of a preferred form of amplifier and multiplexing circuit utilizable in the invention, which circuit enables detector signal channel calibration as an incident of patient examination.

A preferred circuit arrangement for use as the amplifier and multiplexing block 98 of FIG. 4, is shown in FIG. 5. The circuit shown therein is particularly useful in addressing two problems arising in connection with the present apparatus. Firstly, because of the wide variation in path densities which may typically be encountered during scanning of a bodily portion (including e.g. the fact that certain of the "edge" rays of fan beam 52 may pass outside the body all together, or pass only partially through same), a wide variation in outputs from the detectors 56 occurs. These levels further are very low to begin with. In a typical instance for example the range of detector outputs which may be encountered in a typical situation can range from 1 pA to 300 nA. This in turn tends to require a signal processing circuit that is not only very sensitive, but is also relatively uniformly responsive to the very wide signal variation range indicated.

In addition a further significant problem encountered in the present apparatus arises by virtue of drift—which occurs in the detector signal processing channels during the course of extended operation of the present apparatus. Because the effects of drift may vary from channel to channel, an imbalance can develop over the extended work period, with resulting erroneous readings in the data. The circuit of FIG. 5 permits for full treatment of both of these aforementioned problems; and in particular permits for recalibration of the various detector signal processing channels as an incident to the patient scan operation.

Initially it should be pointed out that at the beginning of a day's operation involving apparatus of the present type, the plurality of channels proceeding from the detector array 56 are calibrated. In particular a so-called "phantom", i.e. a block of material of known density such as uniform polyethylene, is initially placed in the apparatus and a test scan run is effected through such material utilizing the x-ray scan to thereby establish a base line. Effectively the computer 188 is thus utilized to equalize or normalize the gains of the various channels. A measurement is also made of the X-ray beam intensity completely unabsorbed, i.e. this may involve transmission characteristics at the edge of the phantom. The object of this operation is to in effect indicate the absolute intensity value of the x-ray source, for subsequent comparison purposes.

Referring to FIG. 5 showing a representative channel, the output from detector ion chamber 212 is provided during the scan process to an integrator 214, with the output from the integrator proceeding to a sample and hold circuit 216, thence to an analog multiplexer 218, and finally to an A-D converter 220; thence the output from the latter is provided to computer 188. The output from integrator 214 is also seen to be provided via line 222 to a level detector 224. The level detector output in turn, serves as one input to a JK flip flop 226, which is also provided with a crystal reference frequency from source 228. This reference frequency is also provided to the corresponding flip-flops in all other detector channels. The K-gate of the aforementioned flip flop is provided with a "high" level digital signal at 230.

The signal proceeding from ion chamber 212 is integrated at 214, as is indicated by the waveform 232, which actually is a negative-going signal as shown. Upon a sufficiently diminished negative level 234 being achieved, a signal is generated at level detector 224, which actuates flip flop 226 on the next clock pulse then occuring. This in turn provides a pulse to counter 236, which is strobed by latch 238 at the end of each measurement period. The output of the latch is connected to digital multiplexer 240, and thence to computer 188. Each time the signal level 234 is achieved the pulse from flip flop 226, actuates a charge dispenser circuit 242, which includes an FET switch and a constant current source. This effectively resets the integrator to the upper level 244 of waveform 232.

The branch of the FIG. 5 circuit including counter 236, latch 238 and digital multiplexer 240 effectively acts as a course measuring circuit; i.e. the number of counts thereby measured provides a course indication of the output level of detector 212. Similarly the elements 214, 216, 218 and 220 effectively constitute a "fine" measuring branch for the output proceeding from ion chamber 212. It will, of course, be evident that the arrangement indicated will have a very high dynamic response range.

The circuit of FIG. 5 further, enables a calibration for the purposes aforementioned. In particular it will be noted that high and low reference sources 246 and 248 (common to all detector channels) are provided, which may be connected to the common point 250, i.e. in front of integrator 214, by means of a branch 252 including a high impedance resistance 254. Switching between the high reference 246 and low reference 248 (which may be at ground) is enabled by a control line 256 to computer 188. The switch 258 may in practice constitute a reed switch, with the control element therefor being actuated by the computer.

The operation of the aforementioned circuit in the calibration procedure may be best understood by noting that with a patient in place as e.g. indicated in FIG. 1, a single cycle of rotation is effected, i.e. with the x-ray source 56 on, as has previously been discussed. Subsequently, with the x-ray off, i.e. at the completion of the given cycle, further rotation is effected, which constitutes a calibration run. During this calibration run switch 258 is sequenced between the high reference 246 and low reference 248 positions. In consequence of this operation, the relative gain is measured in each of the plurality of channels, i.e. the relative gain is determined as between the high reference input on the one hand and the low reference input on the other. The computer thereupon adjusts the effective gain for the various channels so as to equalize or normalize same, i.e. to achieve the same normalization as was effected at the beginning of the day's operations, so that adjacent channels are effectively producing the same relative gain—when on the one hand a high reference, and on the other hand a low reference, input is used. This of course need not involve any adjustment of the electronic components in the channels, but merely a modification of the numerical values interpreted at the computer.

An edge measurement is also made—as has been previously discussed in connection with initial calibration at the beginning of a day's operation—, the purpose of this operation being to enable a comparison between the absolute intensity of the x-ray source at the time of initiating operations and at the calibration time, thereby enabling the computer to effect adjustment for changes in source intensity as well.

In addition to performing the operations indicated, the computer also determines the precise multiplying factor as between the two outputs, i.e. from A-D converter 220 and from digital multiplexer 240. This is effected by utilizing as high reference 246 a signal which on the average yields $N+\frac{1}{2}$ pulses from charge dispenser 242. Comparison of the two outputs then provides an indication of the said multiplying factor to thereby enable precise compensation of the detector outputs by the computer.

All of the aforementioned calibration procedures may be effected with patient 54 in place; or just prior or subsequent to the patient scan. The procedures may be manually initiated by operator insertion of a request at logic 108, or the sequence may automatically proceed under control logic 108.

It has previously been pointed out that an important aspect of the present invention and, one which enables certain features of the invention already described—including continuous rotation of assembly 16, is the use of a slip ring assembly 70 to enable both the excitation and control interconnections to the x-ray tube source, and as well the various interconnections utilized to lead other control inputs into apparatus 10, and data outputs outwardly from apparatus 10. The slip ring assembly 70 has been generally discussed heretofore, in connection with FIG. 3. Further details of the slip ring assembly are set forth in connection firstly with FIG. 6 which is a plan view taken in the direction 6—6 of FIG. 3, and in the longitudinal cross-sectional view of FIG. 7, which is taken along the line 7—7 of FIG. 6.

Figure 6:
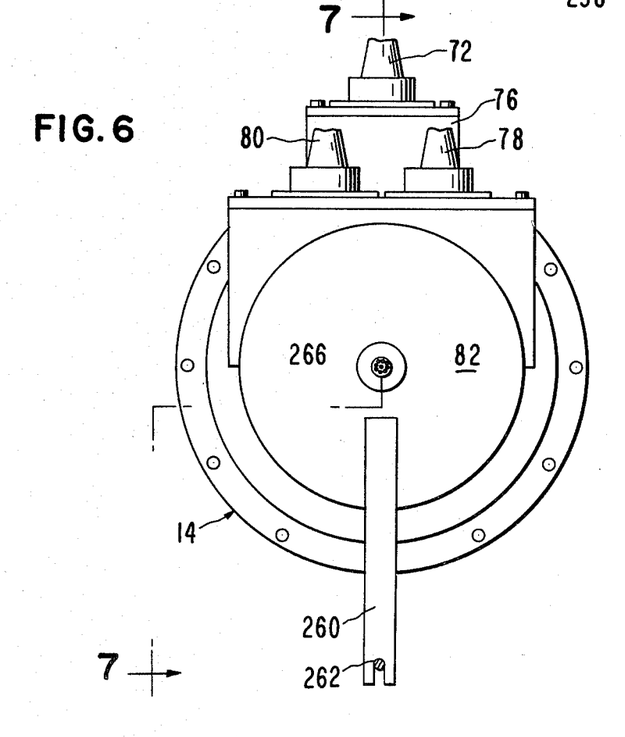
FIG. 6 is a front end view of the slip ring assembly portion of the FIGS. 1 through 3 apparatus, the view being taken in the direction 6—6 of FIG. 3.
Figure 7:
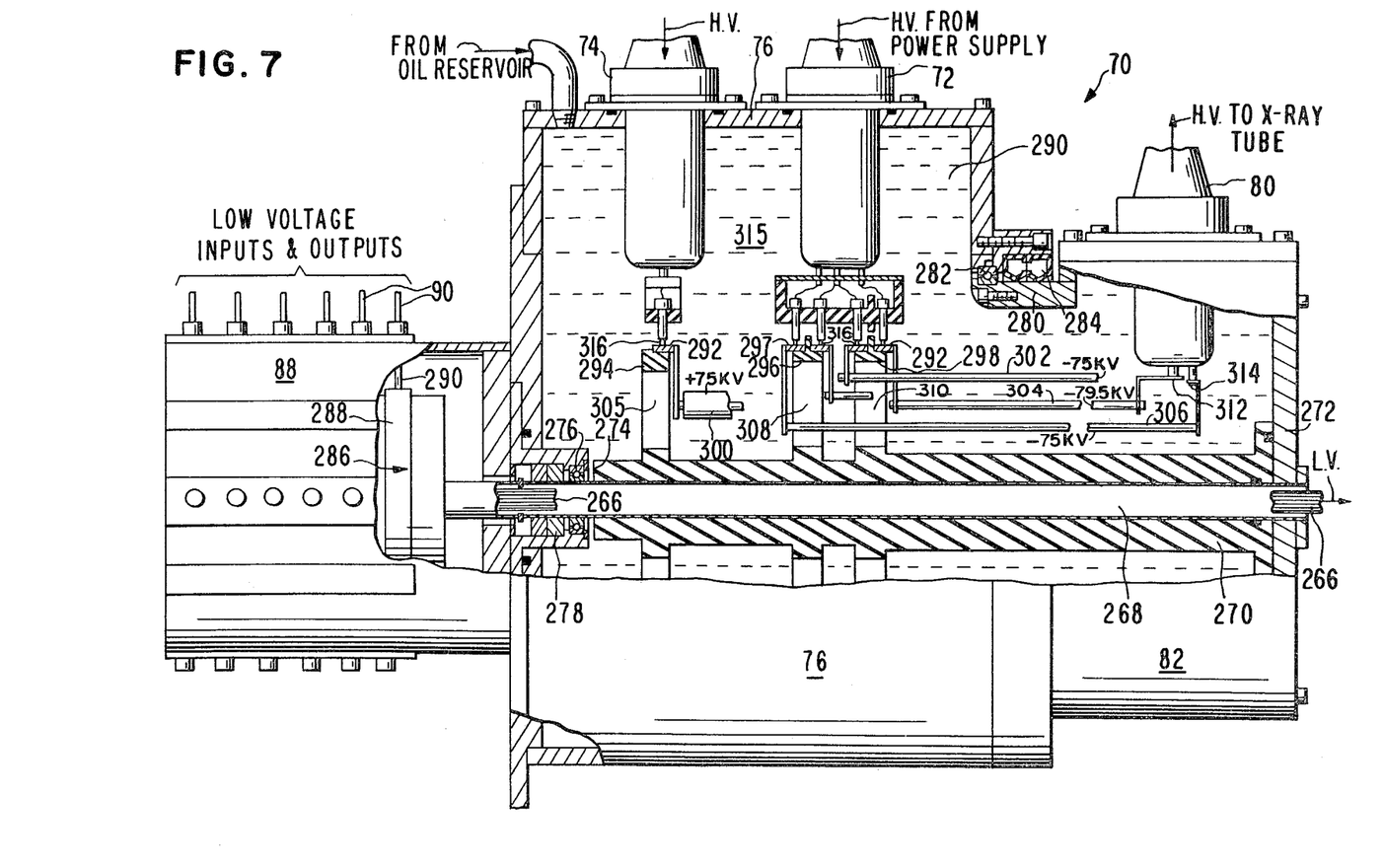
FIG. 7 is an elevational view, partially sectioned and broken-away, of the apparatus depicted in FIG. 6, the view being taken along the line 7—7 of FIG. 6.

Referring firstly to FIG. 6, it is seen that rotation of portion 82 is effected commonly with the cylinder 22 by means of a link 260 which is secured to portion 82 and engages a pin 262 which projects from the rearward side 264 of cylinder 22. In FIG. 7, the high voltage inputs 72 and 74 from power supply 122 can be seen, as well as the high voltage output 80 which proceeds to x-ray source 30. Also, a series of connectors 90 for the low voltage inputs and outputs can be seen. These are mounted to the portion 88, which as already has been indicated, is a stationary member; i.e. this is to say that the various lines proceeding from connectors 90 are in turn connected to the control and image reconstruction station 20—or in some instances to low voltage inputs such as from x-ray starter 120, and to A.C. power for the signal processing and conditioning circuits on assembly 16.

Referring principally now, to the cross-sectional view of FIG. 7, it should initially be pointed out that the slip ring structures provided at the portion 88 of the assembly 70 are set forth in only limited detail herein, in that these are of a conventional type heretofore utilized to enable low voltage inputs to be transmitted in rotating machinery environments. It will, however, be noted in that connection, that the series of low voltage cables 266 proceed directly down the tube 268 of assembly 70. Tube 268 is mounted within a center member 270 of an insulating material such as Lucite or the like, which proceeds from the front plate 272 to a point 274 proximate the rear bearing support 276 and bearing support rings 278. Front plate 272, together with central member 270 and ring 280, all rotate with assembly 16, as does, of course, the high voltage cable connectors 78 and 80. As is evident as well by comparing FIG. 3, the portion 76 does not rotate, which portion carries the previously mentioned high voltage cable input connectors 74 and 76, i.e. these connectors receive the high voltage cable supplies from the x-ray power source associated with the present tomographic system 92. Electrical interconnection between cables 266 and connectors 90 is enabled by a conventional rotor 286 which carries slip rings 288 which contact brushes 290, in turn in electrical connection with connectors 90 (only sixteen required for output from the 301 detectors).

The rotation mentioned between ring 280 and the various other elements of portion 82 on the one hand, and of portion 76 on the other, are enabled by a bearing 282 which is present between the two said portions. An oil seal 284 is also provided between these portions in that the entire interior of portions 76 and 82 of assembly 70, i.e. interior 290 is filled with oil 315 or similar material having very high insulating characteristics.

The high voltage slip ring electrical contacts are seen to consist of a series of ring contacts 292, which are secured to flanges 294, 296 and 298 on center member 270 (which flanges of course are also insulating). From these contacts, a series of electrical conduits 300, 302, 304 and 306 extend, passing through appropriate openings 305, 308 and 310 in the flanges 294, 296 and 298, and thence connecting at such points as 312 and 314 to the high voltage connectors 78 and 80 proceeding to the x-ray tube. The various excitation potentials are indicated in the Figure for a representative operation. Contact with the rotating slip rings is effected through a series of brushes 316, which may be of graphite-based or of other composition as is known in the art.

While the present invention has been particularly set forth in terms of specific embodiments thereof, it will be understood in view of the present disclosure, that numerous variations upon the invention are now enabled to those skilled in the art; which variations yet reside within the scope of the present teaching. Accordingly, the invention is to be broadly construed and limited only by the scope and spirit of the claims now appended hereto.

What is claimed is:

1. An apparatus for examining a subject by means of penetrating radiation and providing a digital output signal for use in reconstruction of a representation of the structure residing in a section taken through said subject; said apparatus comprising:

means for causing penetrating radiation to enter said subject at a plurality of locations around said section, and detector means for detecting radiation passing through said section; and signal processing means for receiving the output signals from said detector means and amplifying and converting said signals to digital form;

the improvement wherein:

said signal processing means includes integrator means for integrating the output signals from said detector means, means for resetting said integrator means upon the integrated signal reaching a selected level, means for counting the resets generated by said detector output signal to provide a coarse measure of said output signal, and means for measuring the remaining signal level from said integrator means to provide a fine measurement of said detector output signal, whereby said processing means is relatively sensitive to a wide range of said detector signals.

* * * * *